United States Patent [19]

Castillo et al.

[11] Patent Number: 5,230,697
[45] Date of Patent: Jul. 27, 1993

[54] KNEE BRACE

[75] Inventors: James D. Castillo, Santa Maria; Edward L. Castillo, Laguna Hills, both of Calif.

[73] Assignee: Innovation Sports, Inc., a Calif. Corp., Irvine, Calif.

[21] Appl. No.: 694,681

[22] Filed: May 2, 1991

[51] Int. Cl.⁵ .............................................. A61F 5/00
[52] U.S. Cl. ........................................ 602/16; 602/26
[58] Field of Search ............... 128/80 C, 80 R, 80 F, 128/87 R, 88; 602/16, 26, 5

[56] References Cited

U.S. PATENT DOCUMENTS

| | | |
|---|---|---|
| 4,620,532 | 11/1986 | Houswerth .......................... 602/16 |
| 4,791,916 | 12/1988 | Paez . |
| 4,803,975 | 2/1989 | Meyers . |
| 4,854,308 | 8/1989 | Drillio . |
| 4,886,054 | 2/1989 | Castillo et al. . |
| 4,940,044 | 7/1990 | Castillo . |
| 5,063,916 | 11/1991 | France et al. . |

FOREIGN PATENT DOCUMENTS 2581859 11/1986 France .
2627381 8/1989 France .

Primary Examiner—Richard J. Apley
Assistant Examiner—Linda C. M. Dvorak
Attorney, Agent, or Firm—Stetina and Brunda

[57] ABSTRACT

A brace for supporting a knee joint is disclosed which is specifically adapted for use in athletic, i.e. sports, applications. The brace is formed by a pair of frame members disposed on opposite sides of the knee joint which are pivotally connected adjacent one end by way of ratio-swing hinge members. Attached to the inner surface of the lower frame member is a tibia pad which is used to provide a firm interface between the lower frame member and the portion of the knee joint adjacent the crest of the tibia. Means are additionally provided to adjust the position of the tibia pad relative to the knee joint. The brace further includes a patella cap which is positionable over the knee cap of the user.

12 Claims, 2 Drawing Sheets

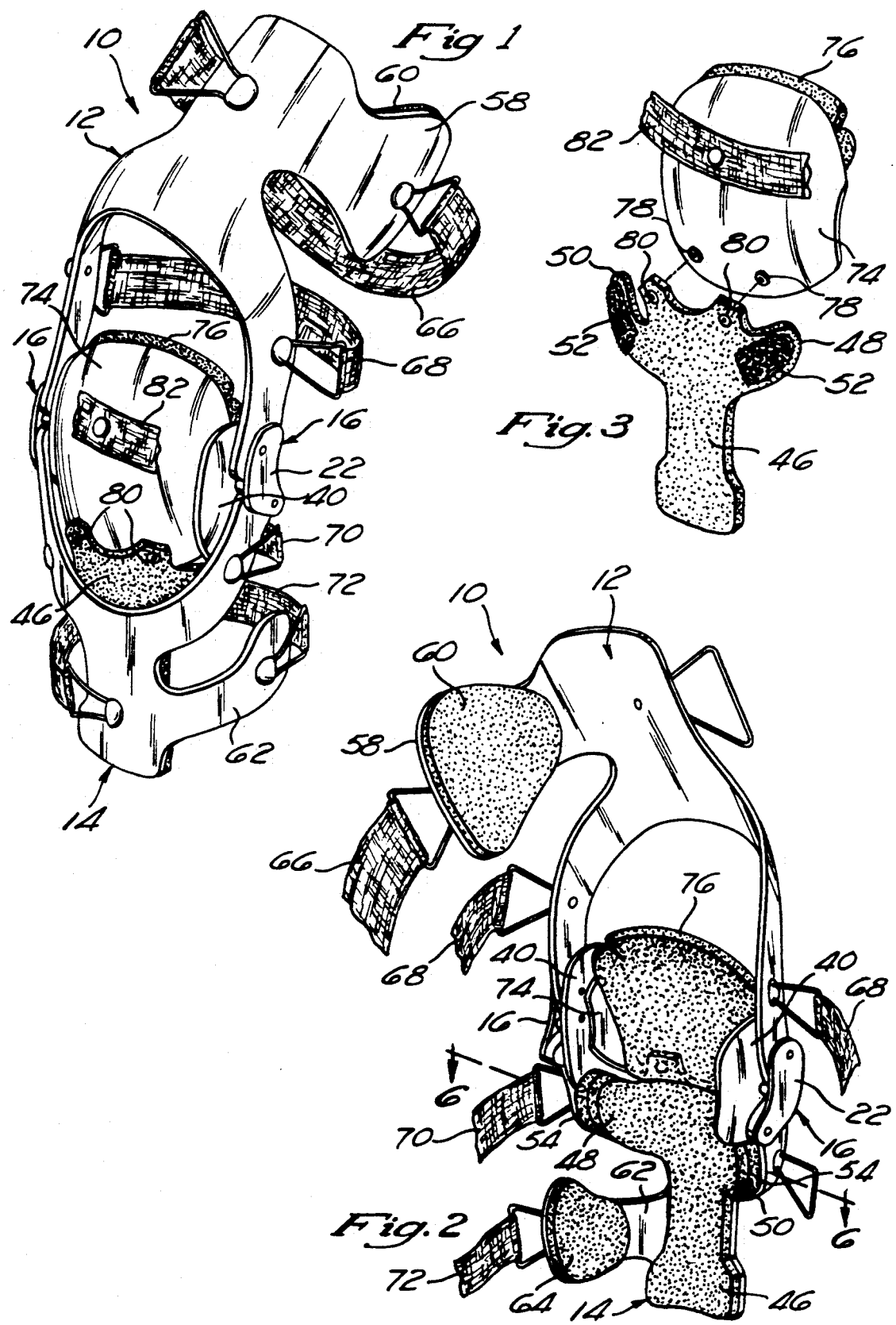

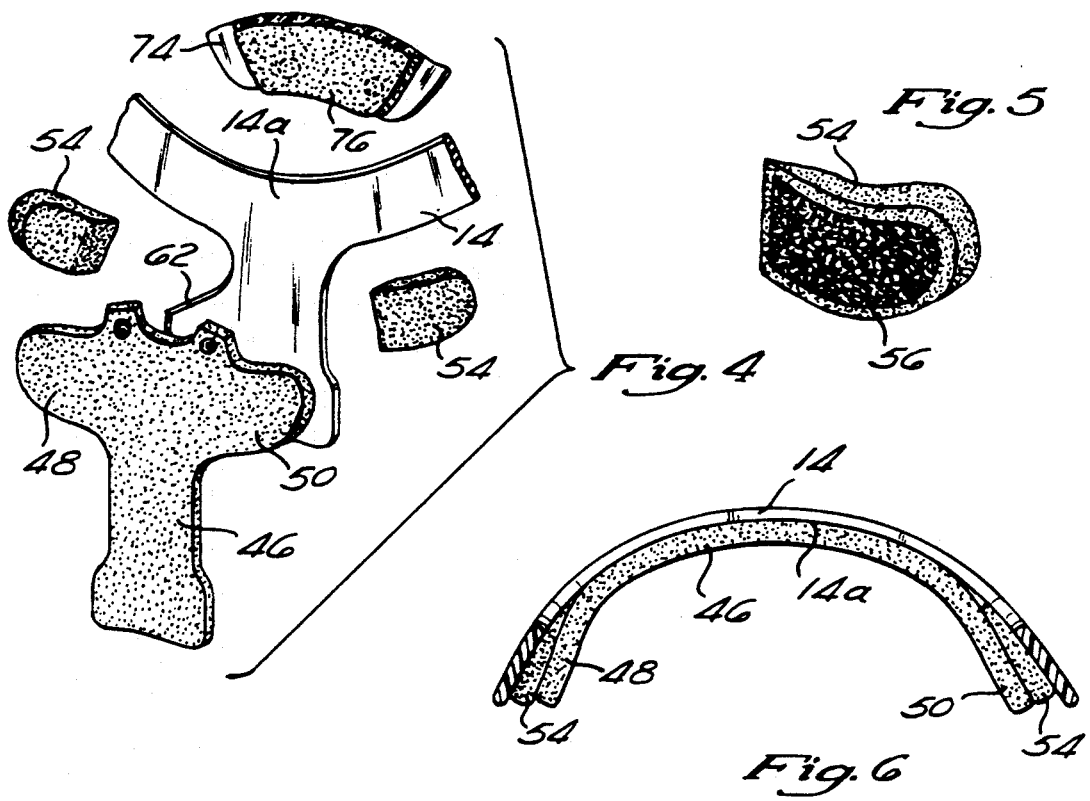
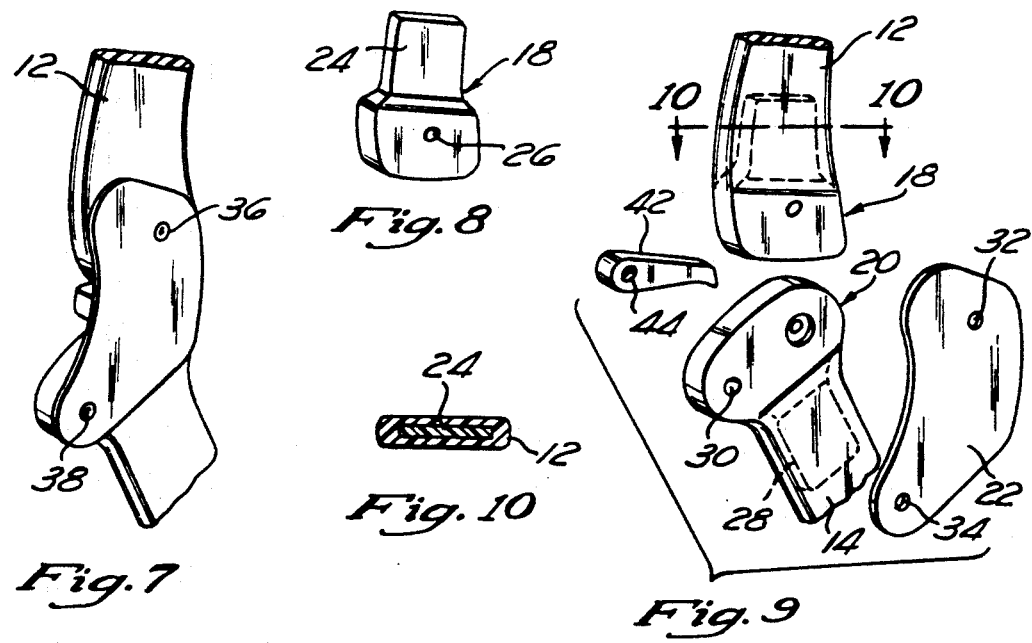

KNEE BRACE

FIELD OF THE INVENTION

The present invention relates to braces for supporting joints, and more particularly to a knee brace specifically adapted for use in athletic, i.e. sports, applications.

BACKGROUND OF THE INVENTION

As is well known, the knee joint, although frequently considered a hinge joint, actually comprises two joints, lateral and medial, between the femur and tibia, and one arthrodial joint between the patella and femur. The primary movements of the knee comprise flexion, i.e., rearward rotational movement of the tibia relative the femur, and extension, i.e. forward rotational movement of the tibia relative the femur.

The flexion and extension movements of the knee joint are not simply pivotal movements about a fixed axis. During flexion, the axis around which movement takes place shifts backward, and during extension it shifts forward. This is different from a more typical hinge joint, such as an elbow, where the axis of rotation does not shift. As full extension is reached, the tibia is rotated inward or rearward and the joint in effect is disposed in a "locked" position with the ligaments taut. This gives the joint greater stability in the extended position. As flexion is initiated, the tibia initially lowers or moves downwardly with the small external rotation of the tibia which "unlooks" the joint and subsequently the tibia rotates or rolls about the joint to full flexion. Accordingly, the initial unlocking of the knee joint during flexion precedes actual full rotation of the knee.

Due to the above complexity of knee movement, for a knee brace to more fully support the knee joint of the user and facilitate rehabilitation and/or prevent re-injury of an injured knee joint, the brace must more closely analogize the movement of the knee than a simple hinge mechanism. Additionally, with specific relation to athletic or sports applications, the requirement for such analogized movement becomes acute. Further, for such sports applications, a knee brace must be relatively lightweight to avoid over-constriction which reduces success in the athletic endeavor, yet possess sufficient structural strength to adequately support the knee joint during impact thereupon.

In recognizing the need for an effective sports knee brace, various knee braces have been introduced into the marketplace. Such contemporary knee braces, however, have generally failed to provide the precise simulation of knee joint movement as described above or have comprised relatively heavy, bulky apparatus, thereby detracting from the user's athletic endeavor. Further, such contemporary designs have typically failed to possess sufficient structural integrity to prevent re-injury of the knee joint as may be occasioned by impact to the knee joint during physical sport endeavors.

Additionally, most contemporary sports braces have further been deficient in that the brace is not constructed in a manner so as to provide a consistently firm interface between the knee brace and the portion of the knee joint adjacent the crest of the tibia. This particular area of the knee joint typically becomes swollen after surgery or the occurrence of other trauma to the knee. As such, when the user is initially fitted with a knee brace, the knee brace is typically sized to conform to the shape of the knee at the time of the fitting. Thus, as the swelling of the knee subsides, oftentimes a gap is formed between the brace and the knee thereby necessitating that remedial measures be taken on the knee brace to alleviate the gap and achieve a more precise fit of the brace to the knee. Finally, most contemporary sports braces have further been deficient in their lack of providing suitable protection to the patella portion of the knee joint.

SUMMARY OF THE INVENTION

The present invention specifically addresses and alleviates the above-referenced deficiencies associated with the prior art. More particularly, the present invention comprises a brace for supporting a knee joint which, although not limited thereto, is specifically adapted for use in athletic, i.e. sports, applications.

The brace is formed by a pair of frame members disposed on opposite sides of the knee joint which are pivotally connected adjacent one end thereof by way of ratio-swing hinge members. The ratio-swing hinge members are specifically designed to closely simulate rotational movement of the tibia relative the femur whereby the pivot point of the hinge varies or changes during rotational movement of the tibia relative the femur. As such, the knee brace of the present invention closely simulates normal knee movement, thereby enhancing rehabilitation and preventing injury to the knee during use. In the preferred embodiment, each of the frame members is formed of a high strength, lightweight composite material possessing sufficient strength to adequately support the knee joint even during physical impact associated with sports endeavors, yet be sufficiently lightweight so as not to deter from performance of the physical endeavor. Additionally, the hinge members are formed to include metal inserts thereon which are received directly into the frame members so as to impart greater strength and structural rigidity to the brace.

In the preferred embodiment, the lower frame member includes a tibia pad which is removably attachable to the inner surface thereof. The tibia pad is used to provide a firm interface between the lower frame member and the portion of the knee joint adjacent the crest of the tibia. One or more wedge pads are also provided which are removably insertable between the inner surface of the lower frame member and the tibia pad. The wedge pads are adapted to adjust the positioning of the tibia pad relative to the knee joint so that the tibia pad is always firmly interfaced thereto. As such, the knee brace of the present invention is adapted to provide a firm interface between the brace and the knee irrespective of the degree of knee swelling without the necessity of performing time-consuming and costly remedial operations to the structure of the brace.

The present invention additionally incorporates a patella cup which is removably attachable to the upper portion of the tibia pad. The patella cup is oriented within the knee brace in a manner so as to cover the knee cap of the knee joint, thereby protecting it during sports endeavors.

So as not to hamper the physical endeavor yet prevent any hyper-extension of the knee joint during use, the brace of the present invention incorporates a unique stop mechanism into the ratio-swing hinges of the frame members. In the preferred embodiment, the stop mechanism comprises differing sized stop inserts which may be rapidly inserted into the hinges to restrict extension without restricting flexion of the knee joint. Preferably, the stop inserts are formed as progressively sized elements which serve to limit extension in varying degree segments, such as five degrees, ten degrees, fifteen degrees, and twenty degrees. As such, during rehabilitation of the knee, differing stop inserts may be progressively utilized to allow greater extension as desired. Additionally, first and second condylar pads are connected to the hinge members and are used for providing a cushion between the lateral and medial aspects of the knee joint and the hinge members.

The present invention also incorporates a plurality of strap members which are attached directly to the frame members and serve to maintain the knee brace upon the leg of the user.

BRIEF DESCRIPTION OF THE DRAWINGS

These as well as other features of the present invention will become more apparent upon reference to the drawings wherein:

FIG. 1 is a front perspective view of the knee brace of the present invention;

FIG. 2 is a rear perspective view of the knee brace of the present invention;

FIG. 3 is a front perspective view of the tibia pad and patella cup of the present invention, illustrating the manner in which they are interfaced to each other;

FIG. 4 is an exploded view illustrating the components used to adjust the position of the tibia pad relative to the knee joint;

FIG. 5 is a perspective view of a wedge pad illustrated in FIG. 4;

FIG. 6 is a cross-sectional view taken along line 6—6 of FIG. 2;

FIG. 7 is partial perspective view of a ratio-swing hinge as interfaced to the frame members;

FIG. 8 is a perspective view of the upper hinge component of a ratio-swing hinge;

FIG. 9 is an exploded view illustrating the components comprising a ratio-swing hinge and further depicting the manner in which the upper and lower hinge components are received into the upper and lower frame members; and FIG. 10 is a cross-sectional view taken along line 10—10 of FIG. 9.

DETAILED DESCRIPTION OF THE PREFERRED EMBODIMENT

The description set forth below in connection with the appended drawings is intended merely as a description of the presently preferred embodiment of the invention, and is not intended to represent the only form in which the present invention may be utilized. The description sets forth the functions and structural elements of the invention in connection with the illustrated preferred embodiment. It will be understood however that the same or equivalent functions and advantages of the present invention may be accomplished by different embodiments which are encompassed within the spirit and scope of the present invention.

Referring to the drawings, the knee brace 10 of the present invention, specifically adapted for athletic, i.e. sports, applications, is depicted. For purposes of illustration, the knee brace 10 is illustrated in a left-leg embodiment which is adapted to be worn upon the left leg of a user. However, it will be recognized that the invention is additionally applicable to right-leg embodiments with the structure of the brace 10 being the same but reversed in orientation. As best shown in FIGS. 1 and 2, the knee brace 10 is composed of an upper frame member 12 and a lower frame member 14. Upper frame member 12 and lower frame member 14 each have a generally Y-shaped configuration and are disposed in an inverted relative orientation and positionable on opposite sides of the knee joint of a user. In the preferred embodiment, upper frame member 12 and lower frame member 14 are formed from a fiber reinforced composite material having sufficient rigidity to withstand impact forces encountered during physical sport endeavors yet be sufficiently light in weight so as not to impair the physical sport activity. However, other materials possessing sufficient strength and rigidity are contemplated herein.

The upper frame member 12 and the lower frame member 14 are pivotally connected to one another by a pair of ratio-swing hinges 16, each composed generally of an upper hinge component 18 and a lower hinge component 20 which are interconnected by an exterior plate member 22. Referring now to FIGS. 7-10, upper hinge component 18 includes an upper insert portion 24 formed thereon and a first aperture 26 disposed therein. Similarly, lower hinge component 20 includes a lower insert portion 28 formed thereon and a second aperture 30 disposed therein. In the preferred embodiment, during the construction of upper frame member 12, the fiber-reinforced composite materials comprising upper frame member 12 are laminated directly to and about the upper insert portion 24 of upper hinge component 18. Thus, upper insert portion 24 is received within and integrally connected to upper frame member 12. This method of interconnection is particularly illustrated in FIGS. 9 and 10. Likewise, the lower insert portion 28 of lower hinge component 20 is received within and integrally connected to the lower frame member 14 in the same manner as previously described with respect to upper hinge component 18. As can be appreciated, this manner of interfacing upper hinge component 18 and lower hinge component 20 to upper frame member 12 and lower frame member 14, respectively, provides knee brace 10 with substantially increased structural rigidity. Disposed within the plate member 22 is a third aperture 32 and a fourth aperture 34. Plate member 22 is pivotally mounted to upper hinge component 18 and lower hinge component 20 and hence upper frame member 12 and lower frame member 14 via pivot pins 36 and 38, respectively. In this regard, pivot pin 3 is received into the coaxially aligned apertures 26 and 32 and pivot pin 38 is received into the coaxially aligned apertures 30 and 34. Due to the positioning of the pivot pins 36 and 38 upon the plate member 22 and frame members 12 and 14, the hinges 16 provide a ratio-swing movement between the frame members 12 and 14 as the frame members 12 and 14 are articulated relative one another.

As seen in FIGS. 1 and 2, attached to upper hinge component 18 and lower hinge component 20 are condylar pads 40. In the preferred embodiment, condylar pads 40 are connected to the hinges 16 to provide a cushion between the lateral and medial aspects of the knee joint and the hinges 16. Additionally, the ratio-swing hinges 16 are specifically designed to mount a stop member insert 42 between the upper hinge component 18 and the lower hinge component 20. In the preferred embodiment, the stop member insert 42 comprises an elongate member which is retained between exterior plate member 22 and a condylar pad 40 by way of a threaded aperture 44 disposed therein which is adapted to receive a screw extending through a condylar pad 40. The effective width of the stop member 42 is sized as desired to form a physical stop or barrier which prohibits relative movement between the upper frame member 12 and the lower frame member 14 in extension movement of the knee yet insures free movement between the frame members 12 and 14 in flexion. In the preferred embodiment, the effective width of the stop member insert 42 may be varied by supplying differing-sized stop member inserts 42 with the brace 10, with the differing-sized stop member inserts 42 being sized to progressively limit the degree of extension of the knee, i.e. five-degree extension, ten-degree extension, fifteen-degree extension, etc. In this respect, stop member 42 is removed simply by removing the screw from condylar pad 40. As such, the present invention accommodates rehabilitation and prevents hyperextension of the knee by allowing a user to progressively increase the extension allowed by the knee brace 10 merely by inserting differing-sized stop member inserts 42 within the ratio-swing hinges 16.

A more thorough description of the structure and operation of the ratio-swing hinges 16 is disclosed in U.S. Pat. No. 4,940,044, issued Jul. 10, 1990, and assigned to the assignee of the subject application, the disclosure of which is expressly incorporated herein by reference. The use of the ratio-swing hinges 16 allows relative movement of the upper frame member 12 and lower frame member 14 in a regulated manner varying pivot axis which simulates normal knee movement wherein during initial movement of the tibia relative the femur in flexion, the tibia slightly lowers to "unlock" the knee joint and once "unlocked" subsequently pivots rapidly backward in flexion. In the preferred embodiment, the upper hinge component 18, lower hinge component 20, and stop members 42 are formed of plastic, though it will be appreciated that other materials may be utilized. Additionally, the plate member 22 is preferably formed of stainless steel. Although in the preferred embodiment, the present invention utilizes the ratio-swing hinges 16, those skilled in the art will recognize that other hinge designs may be substituted therefor and are contemplated herein.

Attached to the inner surface 14a of lower frame member 14 is a tibia pad 46. Tibia pad 46, which is preferably constructed from foam rubber material, has a generally T-shaped configuration. In the preferred embodiment, tibia pad 46 is used to provide a firm interface between the lower frame member 14 and the portion of the knee joint adjacent the crest of the tibia. As previously discussed, oftentimes the knee of the user is affected with post-surgical or post-trauma swelling when the knee brace 10 is fitted thereto. During the initial fitting of the knee brace 10 to the user, tibia pad 46 is firmly abutted against the swollen knee. However, as the swelling of the knee decreases, a gap between tibia pad 46 and the portion of the knee joint adjacent the crest of the tibia will eventually be formed. As can be appreciated, the formation of such a gap diminishes the snug fit of the knee brace 10 against the leg of a user, thereby decreasing the effectiveness of the knee brace 10. To alleviate this particular problem, means are provided in the present invention to adjust the position of the tibia pad 46 relative to the portion of the knee joint adjacent the crest of the tibia so as to provide a consistently firm interface between the lower frame member 14 and knee joint.

Referring now to FIGS. 4-6, in attaching tibia pad 46 to lower frame member 14, the laterally extending portions 48, 50 of tibia pad 46 are not secured to inner surface 14a. Thus, lateral portions 48, 50 may be pulled away from inner surface 14a. As seen in FIG. 3, the outer surfaces of lateral portions 48, 50, which normally come in contact with inner surface 14a, are covered with velcro patches 52. When it is desired to maintain either or both of lateral portions 48, 50 in an orientation away from inner surface 14a, one or more wedge members 54 may be inserted between lateral portion 48 and/or lateral portion 50 and inner surface 14a. As seen in FIG. 5, each of wedge members 54 includes a velcro patch 56 thereon. Thus, wedge members 54 are maintained in position between lateral portion 48 and/or lateral portion 50 and inner surface 14a through the interconnection of velcro patches 56 to velcro patches 52. As can be appreciated, the further wedge members 54 are inserted toward the vertical portion of tibia pad 46, the greater the degree of separation between lateral portions 48, 50 and inner surface 14a. Thus, through the utilization of wedge members 54, the tibia pad 46 may be incrementally adjusted as desired so as to stay in firm, abutting contact with the portion of the knee joint adjacent the crest of the tibia. In this respect, as the swelling of the knee goes down, the wedge members 54 may be inserted between one or both of the lateral portions 48, 50 so as to retain contact of the tibia pad 46 against the knee. Wedge members 54 are preferably constructed from foam rubber though other materials may be utilized.

As seen in FIGS. 1 and 2, upper frame member 12 is formed to include a first laterally extending portion 58 which is adapted to conform to the lateral aspect of the lower portion of the user's thigh when knee brace 10 is placed upon the leg of the user. Disposed on the inner surface of first laterally extending portion 58 is a first foam rubber pad 60. Similarly, lower frame member 14 is formed to include a second laterally extending portion 62 which is adapted to conform to the lateral aspect of the upper portion of the user's calf when knee brace 10 is attached to the leg of the user. Additionally, second laterally extending portion 62 includes a second foam rubber pad 64 attached to the inner surface thereof.

As shown, the knee brace 10 of the present invention is preferably attached to the user's leg via strap members 66, 68, 70, and 72. Preferably, strap members 66, 68 are attached directly to upper frame member 12 and are adapted to extend about the soft tissue of the user adjacent the femur. Strap members 70 and 72 are preferably attached directly to lower frame member 14 and adapted to extend about the soft tissue of the user adjacent the tibia. Though not shown, to allow adjustment of the strap members 66, 68, 70, and 72 an adjustment member and clasp may be provided on such strap members.

Attached to the upper portion of tibia pad 46 is a patella cup 74. Patella cup 74 is removably attachable to tibia pad 46 and used to cover the knee cap portion of the knee joint when knee brace 10 is attached to the leg of the user. Secured to the inner surface of patella cup 74 is a cup pad 76 preferably constructed from foam rubber. The attachment of patella cup 74 to tibia pad 46 is preferably facilitated by snaps 78 positioned on the outer surface of patella cup 74. Snaps 78 are adapted to be interfaced to snaps 80 connected to tibia pad 46 adjacent the upper edge thereof. As can be appreciated from the aforementioned interconnection method, patella cup 74 is an optional component of knee brace 10 and need not necessarily be included therewith. Patella cup 74 further includes a cup strap 82 attached to the outer surface thereof. Though not shown, in those instances when a patella cup 74 is included with the knee brace 10, cup strap 82 is secured to strap member 68 to aid in maintaining the patella cup 74 over the knee cap of a user.

With the structure defined, the operation of the knee brace 10 of the present invention may be described. Initially, the knee brace 10 is positioned about the user's leg. Initial sizing of the knee brace 10 for the user is facilitated by insuring that the distance between the ratio-swing hinge member 16 is slightly greater than the medial lateral width of the knee joint such that the hinges 16 are disposed on opposite sides of the knee joint in close proximity thereto. Such sizing of the knee brace 10 is preferably facilitated by the specification formation of the upper frame member 12 and lower frame member 14 to conform to the leg of a particular user.

With the proper sized brace 10 chosen and positioned upon the user's leg, the strap members 66 and 68 are firmly affixed about the soft tissue of the user adjacent the femur. Subsequently, the strap members 70 and 72 are tightened in an analogous manner whereby they are securely fastened about the soft tissue of the user's leg adjacent the tibia. Additionally, if a patella cup 74 is provided within the knee brace 10, the cup strap 82 is then secured to the strap member 68.

The position of the tibia pad 46 is then adjusted relative to lower frame member 14 so as to be in firm contact with the portion of the knee joint adjacent the crest of the tibia. As such, this particular operation insures a snug fit between the lower frame member 14 and leg of the user. The distance into which the wedge members 54 are inserted between the tibia pad 46 and lower frame member 14 depends upon the desired degree of separation between the tibia pad 46 and lower frame member 14.

Although for purposes of illustration, certain materials, components, and structural embodiments have been depicted, those skilled in the art will recognize that various modifications to the same can be made without departing from the spirit of the present invention, and such modifications are clearly contemplated herein.

What is claimed is:

1. A knee brace comprising:
    an upper frame member sized to be positionable above the knee joint of a user and a lower frame member sized to be positionable below the knee joint of the user, each of said frame members including an end portion configured so as to be disposed laterally on opposite sides of the knee joint when the knee brace is attached to the user's leg and a central portion disposed adjacent the front of the user's leg when the knee brace is attached thereto;
    a pair of hinge members disposed substantially adjacent the knee joint when the knee brace is attached to the user's leg and connected to the end portion of each of said frame members to pivot said frame members about the knee joint;
    a tibia pad removably attachable to an inner surface of said lower frame member to provide a firm interface between said lower frame member and a portion of the knee joint adjacent the crest of the tibia; and
    at least one wedge pad removably insertable between the inner surface of said lower frame member and said tibia pad for adjusting the position of said tibia pad relative to the portion of the knee adjacent the crest of the tibia.

2. The knee brace of claim 1 further comprising a patella cup removably attachable to said tibia pad for covering the knee cap portion of the knee joint.

3. The knee brace of claim 1 wherein each of said frame members has a generally Y-shaped configuration.

4. The knee brace of claim 3 wherein said upper frame member includes a first extension formed thereon to conform to the lateral aspect of the lower portion of the user's thigh.

5. The knee brace of claim 4 wherein said lower frame member includes a second extension formed thereon to conform to the lateral aspect of the upper portion of the user's calf.

6. The knee brace of claim 5 wherein said frame members are formed from a fiber-reinforced composite material.

7. The knee brace of claim 6 further comprising first and second strap members mounted to said upper frame member and extensible about the back of the user's thigh.

8. The knee brace of claim 7 further comprising third and fourth strap members mounted to said lower frame member and extensible about the back of the user's calf.

9. The knee brace of claim 1 wherein said pair of hinge members include metal inserts formed thereon sized and configured to be received into said frame members to facilitate the attachment of said pair of hinge members to said frame members.

10. The knee brace of claim 9 further comprising means formed on said pair of hinge members for regulating the relative pivotal movement of said frame members.

11. The knee brace of claim 10 further comprising means formed on said pair of hinge members for limiting the extension of said pair of frame members.

12. The knee brace of claim 11 further comprising first and second condylar pads connected to said pair of hinge members for providing a cushion between the lateral and medial aspects of the knee joint and said pair of hinge members.

* * * * *